United States Patent [19]

König et al.

[11] Patent Number: 5,559,244

[45] Date of Patent: Sep. 24, 1996

[54] PREPARATION OF 1-(HET) ARYL-3-HYDROXYPYRAZOLES

[75] Inventors: Hartmann König, Heidelberg; Norbert Götz, Worms; Reinhard Kirstgen, Neustadt; Bernd Müller, Frankenthal; Klaus Oberdorf, Heidelberg, all of Germany

[73] Assignee: BASF Aktiengesellschaft, Ludwigshafen, Germany

[21] Appl. No.: 429,322

[22] Filed: Apr. 26, 1995

[30] Foreign Application Priority Data

May 3, 1994 [DE] Germany .................. 44 15 484.4

[51] Int. Cl.⁶ .................. C07D 231/22; C07D 231/14; C07D 231/16; C07D 401/04
[52] U.S. Cl. .................. 548/371.1; 544/238; 544/405; 546/276.1; 548/369.4; 548/368.1
[58] Field of Search .................. 548/369.4, 371.1

[56] References Cited

PUBLICATIONS

Nakamura et al, *Chem. Pharm. Bull.*, vol. 19 (1971) pp. 1389–1394.

*Primary Examiner*—Robert W. Ramsuer
*Attorney, Agent, or Firm*—Keil & Weinkauf

[57] ABSTRACT

A process for preparing 1-(het)aryl-3-hydroxypyrazoles of the formula I

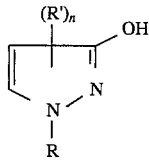

where
R is an unsubst. or subst. aromatic or heteroaromatic radical,
n is 0, 1 or 2 and
R' is a group which is stable under the reaction conditions, from propiolic acid esters of the formula II $$R'—C\equiv C—CO_2R^1 \qquad II$$

where $R^1$ is an alkyl, cycloalkyl or aryl group, and (het)aryl-hydrazines of the formula III $$R—NH—NH_2 \qquad III$$

in a solvent in the presence of a base, which comprises first mixing II and III with one another in a solvent and then treating this mixture with the base at from 0° C. to 60° C. is described.

8 Claims, No Drawings

PREPARATION OF 1-(HET)ARYL-3-HYDROXYPYRAZOLES

The present invention relates to a process for preparing 1-(het)aryl-3-hydroxypyrazoles of the formula I

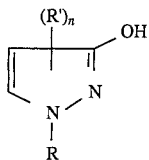

where

R is an unsubst. or subst. aromatic or heteroaromatic radical, n is 0, 1 or 2 and R' is a group which is stable under the reaction conditions, from propiolic acid esters of the formula II

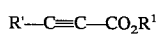

where $R^1$ is an alkyl, cycloalkyl or aryl group, and (het)arylhydrazines of the formula III

in a solvent in the presence of a base.

1-(Het)arylpyrazoles can be obtained by various processes which are summarized, for example, in Bull. Chim. Soc. 1970, 2717, Chem. Heterocyclic Compd. (Engl. Transl.) 16 (1980), 1 or Chem. Ber. 102 (1969), 3260. These processes, however, either have the disadvantage that poorly accessible starting materials are necessary, or that in addition to the 3-hydroxypyrazoles 5-hydroxypyrazoles are formed to a considerable extent or even as the main product.

A further method for the preparation of 3-hydroxypyrazoles from acrylic acid esters and hydrazine derivatives, known from J. Med. Chem. 19 (1976), 715 has the disadvantage that the pyrazolines initially formed have to be oxidized in a further step, such that the preparation comprises at least two reaction steps. According to the process known from Chem. Pharm. Bull. 1971, 1389, 3-hydroxypyrazoles are obtained in the reaction of propiolic acid esters and hydrazines in a solvent in the presence of a base at the boiling point of the solvent. These process conditions, however, can lead to decomposition of the starting materials.

From the experimental results described in Tetrahedron Lett. 1970, 875, it was to be expected that the decomposition of the starting materials could not be avoided by reducing the temperature, since essentially 5-hydroxypyrazoles were formed in the reaction at room temperature.

It is an object of the present invention to provide a simple and gentle process for preparing 1-(het)aryl-3-hydroxypyrazoles, which also makes it possible to prepare sensitive starting materials on a large scale.

We have found that this object is achieved by a process for preparing 1-(het)aryl-3-hydroxypyrazoles of the formula I

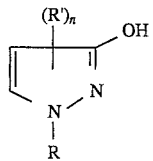

where

R is an unsubst. or subst. aromatic or heteroaromatic radical, n is 0, 1 or 2 and R' is a group which is stable under the reaction conditions, from propiolic acid esters of the formula II

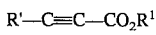

where $R^1$ is an alkyl, cycloalkyl or aryl group, and (het)arylhydrazines of the formula III

in a solvent in the presence of a base, which comprises first mixing II and III with one another in a solvent and then treating this mixture with the base at from 0° C. to 60° C.

For the process according to the invention, it is essential that the starting materials of the formulae II and III are first mixed with one another in the solvent before the base, if appropriate with cooling, is added at from 0° C. to 60° C., preferably 0° C. to 40° C., in particular 20° C. to 40° C.

The molar ratio with respect to the starting materials II and III is in general not critical. It is recommended, however, for completion of the reaction to employ one of the components in an excess. Accordingly from 1 to 3 mol of the propiolic acid ester II, preferably 1 to 1.5 mol, is customarily used per mole of hydrazine III or the corresponding hydrazinium salt.

The amount of base is likewise not critical for the process according to the invention according to present knowledge. Customarily, it is sufficient if the base is used in amounts from 1 to 3 mol per mol of hydrazine III or the corresponding hydrazinium salt, preferably 1.5 to 2.5 mol, in particular 1.8 to 2.2 mol.

The solvents used can basically be all aprotic solvents in which the starting materials II and III dissolve to an adequate extent. Suitable solvents are thus, for example, hydrocarbons or halogenated hydrocarbons such as dichloromethane and carbon tetrachloride or ethers such as diethyl ether, methyl tert-butyl ether and tetrahydrofuran, or mixtures of these. In addition, suitable solvents are also alcohols, where, however, the alcohol must not take part in the reaction. Suitable alcohols are accordingly particularly sterically hindered alcohols, ie. secondary or tertiary alcohols, in particular tertiary alcohols such as tert-butanol.

In general, all non-nucleophilic bases are suitable for the reaction. Tertiary amines {eg. N,N-diisopropyl-N-ethylamine (Hünig's base), 1,5-diazabicyclo[4.3.0]non-5-ene (DBN), 1,4-diazabicyclo[2.2.2]octane (Dabco®) and 1,8-diazabicyclo[5.4.0]undec-7-ene (DBU)} and alkali metal salts of tertiary alcohols having 4 to 8 carbon atoms (eg. potassium tert-butoxide) are particularly suitable.

In principle, all propiolic acid esters II whose ester function can be replaced by hydrazine under the reaction conditions can be used in the reaction. Accordingly, alkyl, cycloalkyl or aryl esters (eg. $C_1$–$C_6$-alkyl, $C_3$–$C_6$-cycloalkyl, phenyl or benzyl) are used. The nature of the group R' is unimportant for the reaction as long as this group does not take part in the reaction, ie. is stable under the reaction conditions. Examples of stable groups which may be mentioned in addition to hydrogen are the following: nitro, cyano, halogen, alkyl, cycloalkyl, haloalkyl, alkoxy, alkylthio, aryl or heteroaryl, the alkyl radicals customarily containing up to 6 C atoms and it being possible for the C-organic radicals in turn to carry further groups which are stable under the reaction conditions.

Suitable (het)arylhydrazines III are compounds in which R is an aromatic or heteroaromatic radical (eg. phenyl, naphthyl, 6-membered ring heteroaromatics such as pyridine, pyridazine, pyrimidine, pyrazine or triazine and 5-membered ring heteroaromatics such as furyl, thienyl, pyrrolyl, isoxazolyl, isothiazolyl, oxazolyl, thiazolyl, pyrazolyl, imidazolyl, oxadiazolyl, thiadiazolyl and triazolyl), it being possible for these groups in turn to carry the groups mentioned above which are stable under the reaction conditions.

In addition to the hydrazines III, the corresponding hydrazinium salts, in particular the salts of inorganic acids (eg. halides such as chlorides and bromides, sulfates, phosphates, hydrogen sulfates, acetates), can be used. These salts behave correspondingly under the reaction conditions if the amount of the base used is higher. Accordingly, using the hydrazinium salts 2 to 4, preferably from 2.5 to 3.5, in particular from 2.8 to 3.2, mol of one of the abovementioned bases are used per mole of hydrazinium salt.

There are obtained by the process according to the invention, in particular, 1-(het)aryl-3-hydroxypyrazoles of the formula I

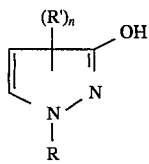

where the radicals and the index have the following meanings:

R is an aromatic or heteroaromatic radical, in particular phenyl, pyridyl, pyrimidyl, pyrazinyl or pyridazinyl, it being possible for these radicals to be partially or completely halogenated (ie. the hydrogen atoms can be replaced completely or partly by identical or different halogen atoms, in particular fluorine and chlorine) and/or to carry one to three of the following groups: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio, and/or it being possible for two adjacent C atoms of these radicals to be bridged via a $C_3$–$C_5$-alkylene, $C_3$–$C_5$-haloalkylene, $C_2$–$C_4$-alkylenoxy, $C_2$–$C_4$-haloalkylenoxy, $C_1$–$C_3$-oxyalkylenoxy or $C_1$–$C_3$-oxyhaloalkylenoxy chain;

n is 0, 1 or 2, in particular 0 (≡R'=hydrogen) or 1, and

R' is nitro, cyano, halogen (in particular fluorine, chlorine and bromine), $C_1$–$C_4$-alkyl (in particular methyl and ethyl), $C_1$–$C_4$-haloalkyl (in particular trifluoromethyl, difluoromethyl and chloromethyl), $C_1$–$C_4$-alkoxy (in particular methoxy or ethoxy), $C_1$–$C_4$-haloalkoxy (in particular trifluoromethoxy), $C_1$–$C_4$-alkylthio (in particular methylthio) and $C_1$–$C_4$-alkoxycarbonyl (in particular methoxycarbonyl and ethoxycarbonyl).

The process according to the invention is particularly suitable for preparing the 1-(het)aryl-3-hydroxypyrazoles I compiled in the following table, which in some cases are known from the literature and in some cases are novel.

| R' | R | R' | R |
|---|---|---|---|
| H | $C_6H_5$ | H | 2,5-$Cl_2$—$C_6H_3$ |
| H | 4-$CH_3$—$C_6H_4$ | H | 3,4-$Cl_2$—$C_6H_3$ |
| H | 3-Cl—$C_6H_4$ | H | 3-$CF_3$—$C_6H_4$ |
| H | 4-Cl—$C_6H_4$ | H | 5-$CF_3$—$C_6H_4$ |
| H | 4-F—$C_6H_4$ | 4-Cl | 4-$CH_3$—$C_6H_4$ |
| H | 2,4-$Cl_2$—$C_6H_3$ | 4-Cl | 4-Cl—$C_6H_4$ |
| H | 2,4-$(CH_3)_2$—$C_6H_3$ | H | 3-$OCH_3$—$C_6H_4$ |
| H | 2-$CH_3$, 4-Cl—$C_6H_3$ | H | 3,4-[$OCF_2O$]—$C_6H_3$ |
| H | 2-Cl—$C_6H_4$ | 4-$CO_2CH_3$ | 4-Cl—$C_6H_4$ |
| H | 3,5-$Cl_2$—$C_6H_3$ | 4-$CO_2CH_3$ | 2,4-$Cl_2$—$C_6H_3$ |
| H | 2,6-$Cl_2$—$C_6H_3$ | H | 4-$CF_3$—$C_6H_4$ |
| H | 2-$CH_3$—$C_6H_4$ | H | pyridin-2-yl |
| H | 3-$CH_3$—$C_6H_4$ | 5-$CH_3$ | $C_6H_5$ |
| H | 4-$OCH_3$—$C_6H_4$ | 5-$CF_3$ | 2,4-$Cl_2$—$C_6H_3$ |
| 4-$NO_2$ | 2,4-$Cl_2$—$C_6H_3$ | 4-Cl | 5-$CF_3$-pyridin-2-yl |
| 4-Cl | 2,4-$Cl_2$—$C_6H_3$ | 4-$CO_2CH_3$ | $C_6H_5$ |
| H | 5-Cl-pyridin-2-yl | H | 4-$OCF_3$—$C_6H_4$ |
| H | 1-pyrazinyl | H | 3-Cl-6-pyridazinyl |

The compounds I obtainable by the process according to the invention are suitable as intermediates in the preparation of dyestuffs or active compounds. They are of particular importance for the synthesis of active compounds of the formula

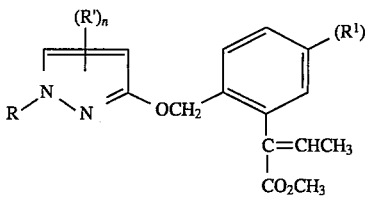

which are described in the parallel application DE Appl. No. . . . for the control of harmful fungi and animal pests.

PROCESS EXAMPLES 1. 3-Hydroxy-1-(4-methoxyphenyl)pyrazole

A solution of 72.7 g of 4-methoxyphenylhydrazine in 700 ml of tert-butanol was treated dropwise at 30° C. with 56.8 g of ethyl propiolate. A total of 118 g of potassium tert-butoxide was then introduced in portions with ice cooling into the mixture thus obtained. After 12 h at 25° C., the solvent was distilled off under reduced pressure and the residue thus obtained was taken up in water. The aqueous solution was washed with dichloromethane and then acidified with conc. acetic acid with cooling to a pH of 9, the product being deposited as a solid. After washing and drying, 60.3 g of the title compound (60% of theory) were obtained; m.p.: 167°–170° C.

2. 3-Hydroxy-1-(4-trifluoromethoxyphenyl)pyrazole

According to the procedure described under 1., 2.43 g of the title compound (23% of theory) were obtained from 8.4 g of 4-trifluoromethoxyphenylhydrazine and 4.7 g of ethyl propiolate (100 ml of tert-butanol, 9.9 g of potassium tert-butoxide); $^1$NMR (DMSO/TMS): 10.40 (s-br, 1H), 8.35 (d, 1H), 7.80 (d, 2H), 7.45 (d, 2H), 5.90 (d, 1H).

3. 3-Hydroxy-1-(5-trifluoromethylpyridin-2-yl)pyrazole

According to the procedure described under 1., 57.2 g of the title compound (58% of theory) were obtained from 76.1 g of 5-trifluoromethylpyridin-2-ylhydrazine and 46.3 g of ethyl propiolate (700 ml of tert-butanol, 96.3 g of potassium tert-butoxide); m.p.: 199°–205° C.

According to the procedure given in Chem. Pharm. Bull. 19 (1971), 1394 in Example XXI, it was not possible to detect any product in the reaction of 8.9 g of 5-trifluoromethylpyridin- 2-ylhydrazine and 8.9 g of methyl propiolate (100 ml of tert-butanol, 11.2 g of potassium tert-butoxide).

4. 3-Hydroxy-1-(2-pyridyl)pyrazole

According to the procedure described under 1., 19.1 g of the title compound (40% of theory) were obtained from 32.7 g of pyridin-2-ylhydrazine and 64.7 g of ethyl propiolate (600 ml of tert-butanol, 134.4 g of potassium tert-butoxide); $^1$NMR (DMSO/TMS): 10.40 (s-br, 1H), 8.40 (m, 2H), 7.90 (m, 1H), 7.70 (d, 1H), 7.20 (m, 1H), 5.90 (d, 1H).

We claim:

1. A process for preparing 1-(het)aryl-3-hydroxypyrazoles of the formula I

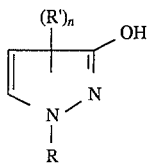

where

R is an unsubst. or subst. aromatic or heteroaromatic radical, n is 1 and

R' is a group which is stable under the reaction conditions, from propiolic acid esters of the formula II

     II where $R^1$ is an alkyl, cycloalkyl or aryl group, and (het)arylhydrazines of the formula III

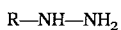     III in a solvent in the presence of a base, which comprises first mixing II and III with one another in a solvent and then treating this mixture with the base at from 0° C. to 60° C.

2. The process of claim 1, wherein the base is a tertiary amine.

3. The process of claim 1, wherein the base is an alkali metal salt of an alcohol having 4 to 8 carbon atoms.

4. The process of claim 1, wherein the reaction is carried out in an aprotic solvent.

5. The process of claim 1, wherein the reaction is carried out in a tertiary alcohol.

6. The process of claim 1, wherein the base is used in an amount from 1 to 3 mol per mole of III.

7. The process of claim 1, wherein, per mole of the compound III, 1 to 3 mol of the compound II are used.

8. The process of claim 1, wherein, instead of the (het)arylhydrazines III, an appropriate hydrazinium salt is used.

* * * * *